(12) United States Patent
Daavettila et al.

(10) Patent No.: US 10,448,941 B2
(45) Date of Patent: *Oct. 22, 2019

(54) SPINAL RETRACTOR WITH RELEASABLE ARMS (71) Applicant: Scanlan International, Inc., St. Paul, MN (US)

(72) Inventors: Jean E. Daavettila, St. Paul, MN (US); Scott E. Jahns, Hudson, WI (US)

(73) Assignee: Scanlan International, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,705

(22) Filed: May 1, 2017

(65) Prior Publication Data

US 2017/0311942 A1    Nov. 2, 2017

Related U.S. Application Data

(60) Provisional application No. 62/329,487, filed on Apr. 29, 2016.

(51) Int. Cl.
*A61B 17/00* (2006.01)
*A61B 17/02* (2006.01)
*A61B 17/28* (2006.01)

(52) U.S. Cl.
CPC ........ *A61B 17/0206* (2013.01); *A61B 17/025* (2013.01); *A61B 17/0293* (2013.01);
(Continued)

(58) Field of Classification Search
CPC .............. A61B 17/0206; A61B 17/025; A61B 17/0293; A61B 17/28; A61B 2017/00367;
(Continued)

(56) References Cited

U.S. PATENT DOCUMENTS 2,863,444 A    12/1958  Winsten
3,965,890 A     6/1976  Gauthier
(Continued)

OTHER PUBLICATIONS

Chadwick, Barry and Toto, Chris. "Radiolucent Structural Materials for Medical Applications." Medical Plastics and Biomaterials, Special Section, 23(6), Jun. 2001, 5 pages
(Continued)

*Primary Examiner* — Pedro Philogene (57) ABSTRACT

A retractor in accordance with embodiments of the invention comprises a retractor element and a retractor arm releasably connectable to the retractor element. A first connector structure on the retractor arm includes a first end portion having a first edge, a first pin slot extending into the first end portion from the first edge, and a first lock well in the first pin slot. A second connector structure on the element includes an end portion having an aperture, the end portion configured to receive the first connector structure at a connected position with the aperture aligned with the first lock well of the first connector structure. The lock includes a first cam and is rotatable between a release position and a lock position. The cam is configured such that (1) when the lock is in the release position the end portion of the second connector structure can be moved to the connected position with respect to the first connector structure with the first cam passing through the first pin slot and into the first lock well of the first connector structure, and (2) when the lock is in the lock position the first cam engages the first end portion of the first connector structure to resist withdrawal of the first end portion of the first connector structure from the second connector structure.

29 Claims, 8 Drawing Sheets

(52) U.S. Cl.
CPC ....... *A61B 17/28* (2013.01); *A61B 2017/0092* (2013.01); *A61B 2017/00367* (2013.01); *A61B 2017/00477* (2013.01); *A61B 2017/0256* (2013.01)

(58) Field of Classification Search
CPC .. A61B 2017/00477; A61B 2017/0092; A61B 2017/0256
USPC .................................................. 600/201–245
See application file for complete search history.

(56) References Cited

U.S. PATENT DOCUMENTS

| | | | |
|---|---|---|---|
| 4,213,451 A | 7/1980 | Swenson | |
| 5,222,279 A | 6/1993 | Frano et al. | |
| 5,512,038 A | 4/1996 | O'Neal et al. | |
| 5,571,072 A * | 11/1996 | Kronner | F16M 11/08 248/279.1 |
| 5,582,577 A | 12/1996 | Lund et al. | |
| 5,794,316 A | 8/1998 | Anscher | |
| 6,042,540 A * | 3/2000 | Johnston | A61B 17/0206 600/213 |
| 6,052,875 A | 4/2000 | Fudaki | |
| 6,263,549 B1 | 7/2001 | Uehara | |
| 8,361,153 B2 * | 1/2013 | Ralph | A61B 17/025 623/17.11 |
| 10,213,192 B2 | 2/2019 | Capote | |
| 2009/0203969 A1 | 8/2009 | Cohen et al. | |
| 2015/0237971 A1 | 8/2015 | Takahashi | |
| 2016/0007982 A1 | 1/2016 | Liu et al. | |
| 2016/0021988 A1 | 1/2016 | Kaneko | |
| 2017/0311940 A1 | 11/2017 | Daavettila et al. | |
| 2017/0311941 A1 | 11/2017 | Daavettila et al. | |

OTHER PUBLICATIONS

Charmant, "Charmant Technology Presentation," Apr. 2016, 8 pages.
Collins, John J. Jr. "Radiolucent Retractor for Operative Coronary Angiography." Department of Surgery, Harvard Medical School and Peter Bent Brigham Hospital, Boston M.A. Accepted for publication Jun. 18, 1976, pp. 478-479.
CTSS. "Cardio-Thoracic Surgery Services: Off-Pumbp Cardiac Surgery." [online]. Retrieved Oct. 18, 2017 using the Internet <http://www.cardiothoracicsurgeryservices.com/21.html>, 2 pages.
Fehling Instruments. "Fehling The Difference: Fehling Instruments Catalog." pp. 1-56, 2016.
Morgan, Gareth J., et al. "Radiolucent Retractor for Angiographic Analysis During Hybrid Congenital Cardiac Procedures." The Journal of Thoracic and Cardiovascular Surgery, 140(5):1195-1196, Nov. 2010.
Final Rejection issued in U.S. Appl. No. 15/581,523, dated Dec. 4, 2018, 12 pages.
Non-Final Rejection issued in U.S. Appl. No. 15/581,523, dated Jun. 12, 2018, 14 pages.
Response to Non-final Office Action filed in U.S. Appl. No. 15/581,523, filed Oct. 12, 2018, 10 pages.
U.S. Appl. No. 15/581,680, filed Apr. 28, 2017, 36 pages.
Utility U.S. Appl. No. 15/581,523, filed Apr. 28, 2017, 42 pages.

* cited by examiner

SPINAL RETRACTOR WITH RELEASABLE ARMS

CROSS REFERENCE TO RELATED APPLICATION

This application claims the benefit of U.S. Provisional Application Ser. No. 62/329,487, filed Apr. 29, 2016 and entitled Spinal Retractor with Releasable Arms Having Cam Locks, which is incorporated herein by reference in its entirety and for all purposes.

FIELD OF THE INVENTION

The invention relates generally to surgical instruments. In particular, embodiments of the invention include spinal and other retractors.

BACKGROUND

Surgical devices such as spinal and other retractors are generally known and commercially available. Devices of these types are often made from metal such as stainless steel or titanium. Materials of these types can block the transmission of x-rays and thereby interfere with or prevent the imaging of anatomical features near the devices. Materials that inhibit the passage of imaging electromagnetic radiation are sometimes called radiodense.

During complex surgical procedures, surgeons often perform radiographic imaging to determine the anatomical and physiological state of the patient. Removing a metal retractor to allow for imaging during such a surgical procedure may take time and disturb the procedure, thereby increasing the risk of complications. Materials that allow the transmission of imaging electromagnetic radiation are sometimes called radiolucent.

There remains a continuing need for improved surgical retractors. In particular, there is a need for retractors that are radiolucent at the surgical site. Any such retractors should be highly functional and capable of being efficiently used.

SUMMARY

Retractors in accordance with embodiments of the invention comprise a retractor element, a retractor arm releasably connectable to the retractor element, a first connector structure on one of the retractor element and the retractor arm, and a second connector structure on the other of the element and the arm. In embodiments the first connector structure includes a first end portion having a first edge, a first pin slot extending into the first end portion, and a first lock well in the first pin slot. The second connector structure includes an end portion having an aperture and a lock in the aperture. The end portion is configured to receive the first connector structure at a connected position with the aperture aligned with the first lock well of the first connector structure. The lock includes a first cam and is rotatable between a release position and a lock position. The first cam is configured such that (1) when the lock is in the release position the end portion of the second connector structure can be moved to the connected position with respect to the first connector structure with the first cam passing through the first pin slot and into the first lock well of the first connector structure, and (2) when the lock is in the lock position the first cam engages the first end portion of the first connector structure to resist withdrawal of the first end portion of the first connector structure from the second connector structure.

In other embodiments the first connector structure includes a first connector end portion having an edge, a pin slot extending into the first connector end portion from the edge, a seat in the pin slot, and an engagement slot in the first connector end portion between the edge and the seat. The second connector structure includes a second connector end portion and first and second spaced-apart joint supports on the second connector end portion. The first and second joint supports are configured to receive the first connector structure therebetween at a connected position. The second connector structure also includes a pin that extends between the first and second joint supports, an engagement flex arm on the first joint support, and an engagement member on the engagement flex arm. The pin, engagement flex arm and engagement member are configured such that during attachment of the second connector structure to the first connector structure (1) the pin passes through the pin slot and into the seat, (2) the engagement flex arm is elastically deflected and the engagement member passes over the first connector end portion between the edge and the engagement slot, and (3) the engagement flex arm springs toward an undeflected position and the engagement member is in the engagement slot when the first and second connector structures are at the connected position.

DETAILED DESCRIPTION

Figure 1:
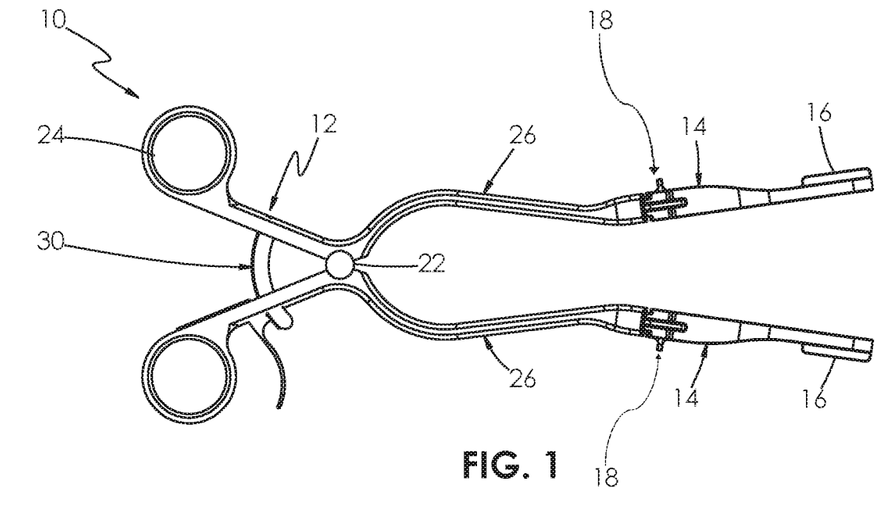
FIG. 1 is an isometric view of an Adson-type spinal tissue/bone retractor in accordance with embodiments of the invention.

A spinal or so-called Adson retractor 10 in accordance with embodiments of the invention can be described generally with reference to FIG. 1. As shown, the retractor 10 includes a handle assembly 12 and a pair of arms 14 having blades 16 that are releasably mounted to the distal end of the handle assembly by connectors 18. The handle assembly 12 includes a pair of handles 20 that are connected by a pivot joint 22. Each handle 20 has a hand-engaging member 24 on its proximal end and an element 26 on its opposite end. Connectors 18 couple the proximal ends of the arms 14 to the distal ends of the handle elements 26. Retractor 10 also includes a clamp 30. During use of the retractor 10, the arms 14 (which can be metal such as titanium or high density and radiolucent polymers) can be selected from sets of differently sized and packaged sterilized arms, removed from the packaging, and mounted to the elements 26 of the handle assembly 12. The connectors 18 are actuated to lock or securably engage the arms 14 to the elements 26. The arms 14 can rotate over a limited range of motion with respect to the elements 26 in the illustrated embodiments of the retractor 10. During surgical procedures, the hand-engaging members 24 can be manually squeezed together or otherwise actuated to spread or open the arms 14 and blades 16. The clamp 30 releasably holds the handle assembly 12 and arms 14 in the selected open position. After the use of the retractor 10, the connectors 18 can be actuated to release the arms 14, and the arms can be removed from the handle elements 26. The previously used arms 14 can be disposed of or sterilized and repackaged for another use.

Other features of retractors 10 in accordance with embodiments of the invention can be described with reference to FIGS. 1-27. Although one arm 14 and element 26 are described below, the arms and elements can be mirror images of one another. The connector 18 of retractor 10 includes a first connector structure 40 on one of the element 26 or arm 14, and a second connector structure 42 on the other of the element or arm. In the illustrated embodiments (e.g., FIGS. 2-7), the first connector structure 40 is on a proximal end of the arm 14 and includes a first end portion 44 having a first edge 46, a first pin slot 48 extending into the first end portion from the first edge, and a first lock well 50 in the first pin slot. The lock well 50 is generally circular in embodiments. In embodiments, the first edge 46 is arcuate, and a surface of the first end portion 44 adjacent to the first edge, first pin slot 48 and first lock well 50 is recessed in the proximal end of the arm 14. The first end portion 44 is generally arcuate or circular in the illustrated embodiment to facilitate the rotational movement and positioning of the arm 14 with respect to the element 26.

In the illustrated embodiments (e.g., FIGS. 8-12), the second connector structure 42 is on the distal end of the element 26 and includes an end portion 60 having an aperture 62 and a lock 70. The end portion 60 is configured to receive the first connector structure 40 at a connected position with the aperture 62 aligned with the first lock well 50 of the first connector structure 40 (e.g., FIG. 24). In embodiments, the end portion 60 is generally arcuate or circular, and mates with the recessed surface of the first end portion 44 of the first connector structure 40 to enable the first connector structure and arm 14 to rotate with respect to the second connector structure 42 and element 26. The first and second connector structures 40 and 42 are thereby configured (e.g., have portions with circular or semicircular shape) to enable at least limited rotation of the arm 14 with respect to the element 26 when the arm and element are connected and the lock 70 is in the lock position.

The lock 70 (e.g., FIGS. 1-17, 22) extends through the aperture 62, and includes a first cam 72 and a handle or knob 76. The lock 70 is retained on the end of the element 26 by washer 81 (e.g., FIG. 18), which is attached to the end of the lock opposite the knob 76. The lock 70 is rotatable between a release position (e.g., FIGS. 19, 20; when the knob 76 is generally parallel with the longitudinal axis of the element 26 in the illustrated embodiment) and a lock position (e.g., FIG. 21; when the knob is generally perpendicular to the longitudinal axis of the element in the illustrated embodiment). The lock 70 and first cam 72 are configured such that (1) when the lock is in the release position, the end portion 60 of the second connector structure 42 can be moved to the connected position with respect to the first connector structure 40 with the first cam passing through the first pin slot 48 and into the first lock well 50 of the first connector structure, and (2) when the lock is in the lock position the first cam engages the first end portion 44 of the first connector structure to resist withdrawal of the first end portion of the first connector structure from the second connector structure. In embodiments, the first pin slot 48 has a first dimension D1 (e.g., FIG. 6), and the first lock well 50 has a diameter D2 (e.g., FIG. 7) that is greater than the first dimension D1 of the first pin slot. The first cam 72 of the lock 70 has first and second diameters D3 and D4 (e.g., FIGS. 16, 17). The first diameter D3 of the first cam 72 is less than the first dimension D1 of the first pin slot 48, such that when the lock 70 is in the release position the flats of the first cam are aligned with the first pin slot and enable the first cam to pass through the first pin slot. The second diameter D4 of the first cam 72 is greater than the first dimension D1 of the first pin slot 48 and optionally slightly less than the diameter D2 of the first lock well 50, to enable the first cam to rotate to the lock position in the first lock well. When the lock 70 is in the lock position, the first cam 72 engages the first end portion 44 of the first connector structure 40, thereby securing the position of the arm 14 by creation of a mechanical interference between the first cam and the first pin slot 48.

At least one of the first and second connector structures 40 or 42 includes stop structure limiting rotation of the lock 70 between the release and lock positions, optionally to a range of rotation of about 90°, in embodiments. For example, in the illustrated embodiment (e.g., FIGS. 6, 24) the stop structure includes one or more tabs such as 74 that extend into the first lock well 50 of the first connector structure 40.

Figure 2:
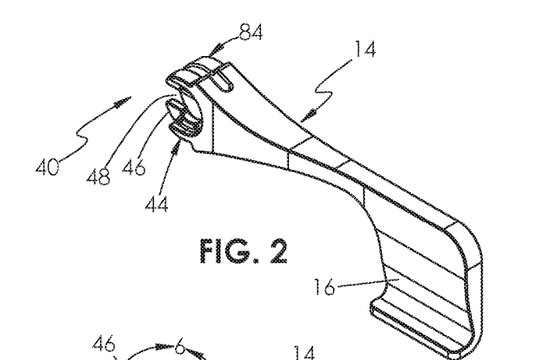
FIG. 2 is an isometric view of an arm of an embodiment of the retractor shown in FIG. 1. The other arm shown in FIG. 1 can be a mirror image of the arm shown in FIG. 2.
Figure 3:
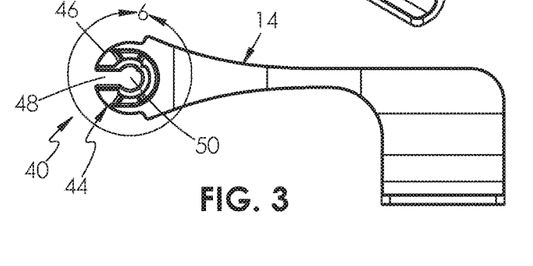
FIG. 3 is a side view of the arm shown in FIG. 2, illustrating a first side shown in FIG. 2.
Figures 4, 27:
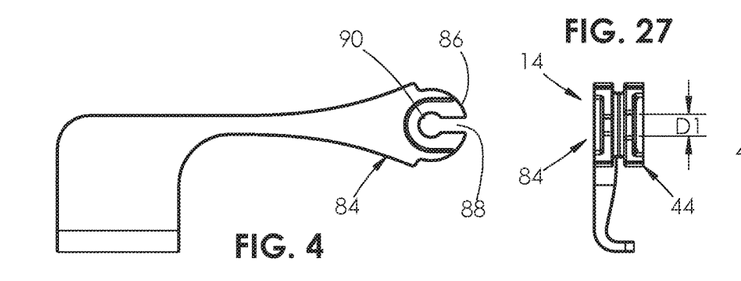
FIG. 4 is a side view of the arm shown in FIG. 2, illustrating a second side opposite the side shown in FIG. 3.
FIG. 27 is an end view of the arm shown in FIG. 3, illustrating the end with the connector structure.
Figure 5:
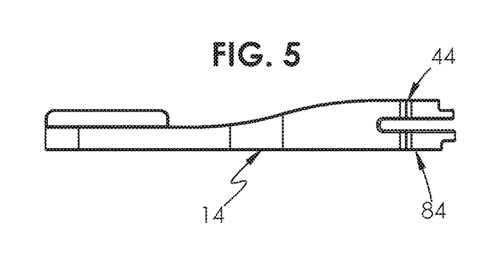
FIG. 5 is a top edge view of the arm shown in FIG. 2, illustrating the edge shown in FIG. 2.
Figure 6:
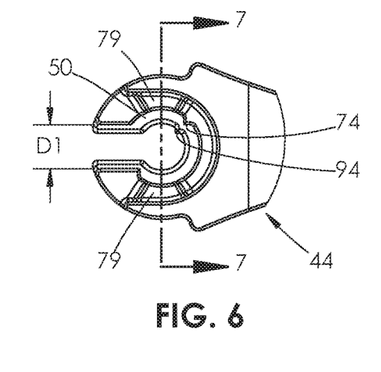
FIG. 6 is a detailed side view of the connector structure on the proximal end of the arm shown in FIG. 3.
Figure 7:
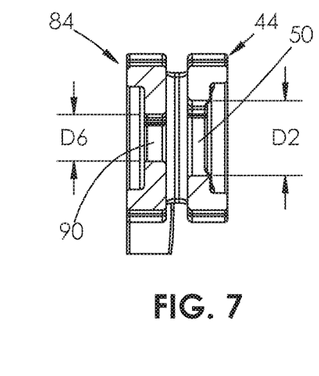
FIG. 7 is a cross sectional view of the connector structure shown in FIG. 6, taken along line 7-7 in FIG. 6.
Figure 8:
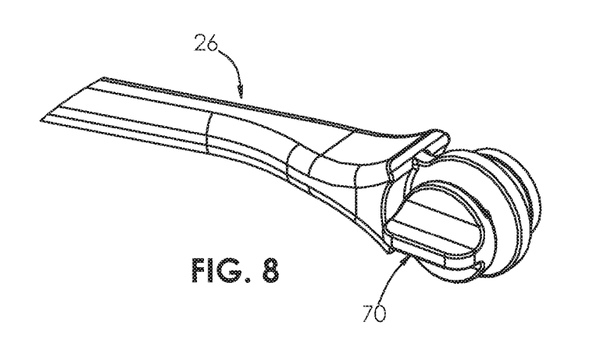
FIG. 8 is an isometric view of an element of the retractor shown in FIG. 1, illustrating the connector structure on the distal end of the element. The other element and connector structure shown in FIG. 1 can be a mirror image of the arm shown in FIG. 8.
Figure 9:
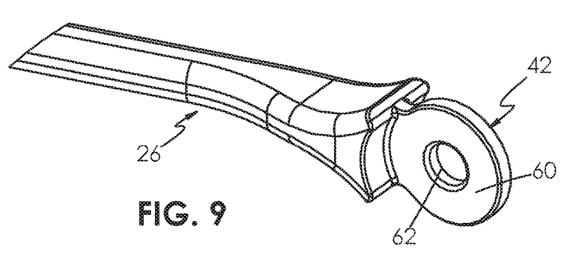
FIG. 9 is an isometric view of the element shown in FIG. 8 with the lock of the connector structure removed to illustrate the end portion of the element.
Figures 10, 11:
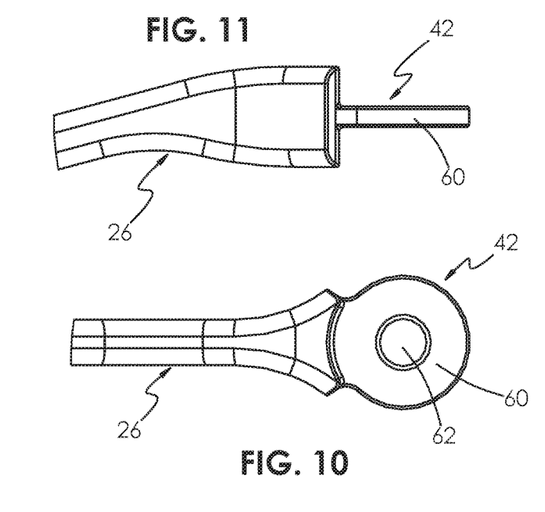
FIG. 10 is a side view of the end portion of the element shown in FIG. 9, illustrating a first side shown in FIG. 9.
FIG. 11 is a top edge view of the arm shown in FIG. 9, illustrating the edge shown in FIG. 9.
Figure 12:
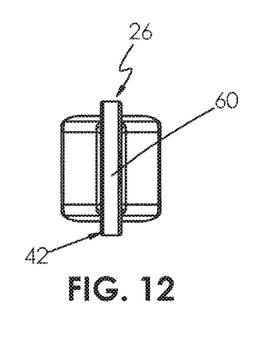
FIG. 12 is an end view of the arm shown in FIG. 9, illustrating the end shown in FIG. 9.

Embodiments of the first connector structure 40 also include a second end portion 84 having a second edge 86 (e.g., FIGS. 2, 4). In embodiments, the second end portion 84 can be generally structurally similar to the first end portion 44. The second end portion 84 is spaced from the first end portion 44 of the first connector structure 40 so as to be on a side of the end portion 60 of the second connector structure 42 opposite the first end portion of the first connector structure when the first connector structure is connected to the second connector structure. A second pin slot 88 extends into the second end portion 84 from the second edge 86 of the second end portion (and optionally parallel with the first pin slot 48 of the first end portion 44). The first connector structure 40 further includes a second lock well 90 in the second pin slot 88. The second lock well 90 is generally circular in the illustrated embodiments. When the lock 70 is in the release position the end portion 60 of the second connector structure 42 can be moved to the connected position with respect to the first connector structure 40, with the lock passing through the second pin slot 88.

Figures 13, 14, 15, 18:
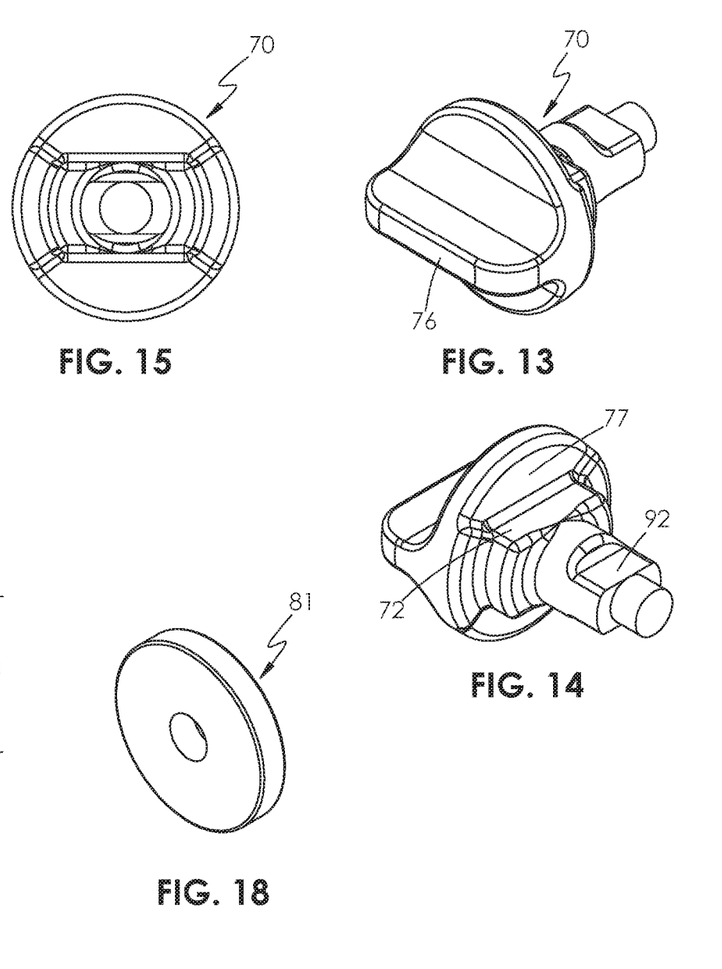
FIG. 13 is an isometric view of the lock of the connector structure shown in FIG. 8, illustrating a first or knob end of the lock.
FIG. 14 is an isometric view of the lock of the connector structure shown in FIG. 8, illustrating a second or cam end of the lock opposite the end shown in FIG. 13.
FIG. 15 is an end view of the lock shown in FIG. 8, illustrating the cam end shown in FIG. 14.
FIG. 18 is an isometric illustration of a washer of the connector structure shown in FIG. 8.
Figure 16:
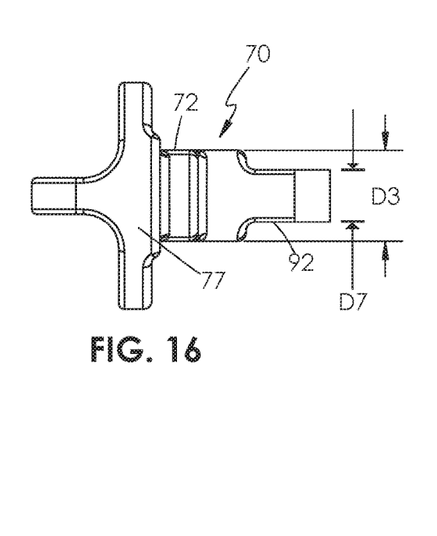
FIG. 16 is a side view of the lock shown in FIG. 13, illustrating a first side of the lock.
Figure 17:
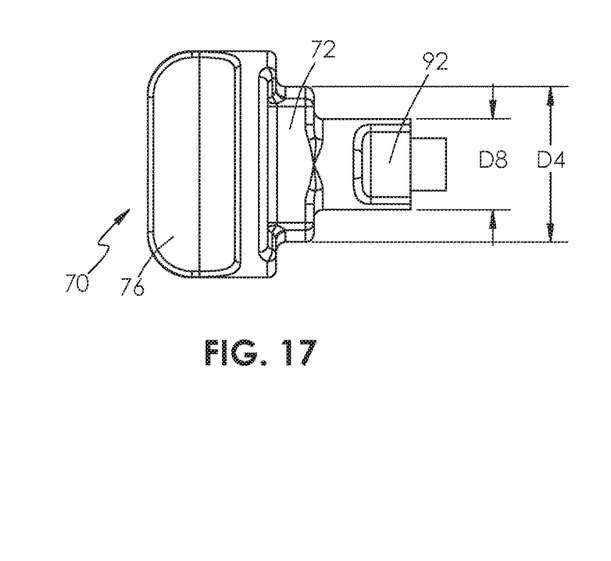
FIG. 17 is a side view of the lock shown in FIG. 13, illustrating a second side offset from the first side shown in FIG. 16 by 90°.
Figure 19:
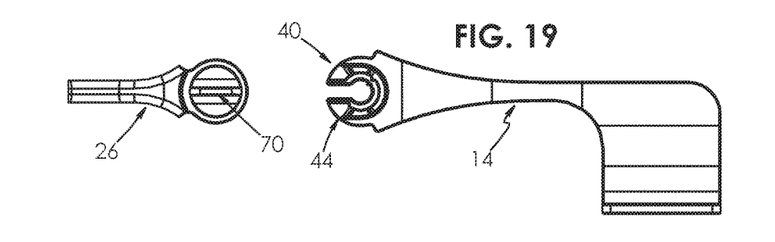
FIG. 19 is a side view of the arm and connector structure shown in FIG. 2 and the element and connector structure shown in FIG. 8 disconnected from one another, illustrating the lock at a release rotation position enabling the arm to be attached to the element.
Figure 20:
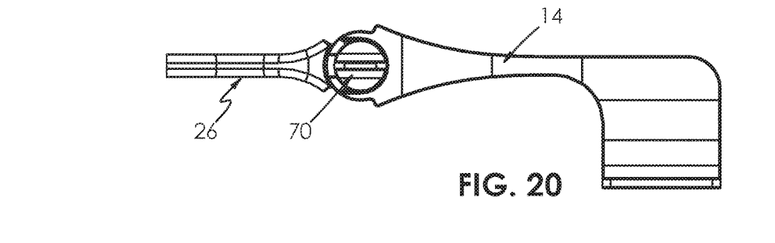
FIG. 20 is a side view of the arm and connector structure and the element and connector structure shown in FIG. 19, with the arm connector structure inserted into the element connector structure, and illustrating the lock at the release rotation position enabling the arm to be attached to and removed from the element.
Figures 21, 22, 23:
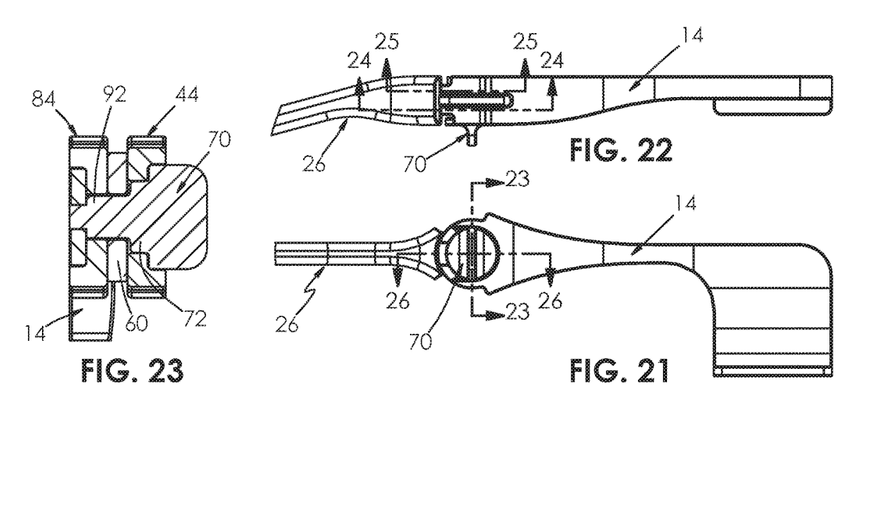
FIG. 21 is a side view of the attached arm and element shown in FIG. 20, illustrating the lock at a locked rotation position locking the arm to the element.
FIG. 22 is a top edge view of the attached arm and element shown in FIG. 21, illustrating the lock at the locked rotation position.
FIG. 23 is a sectional view of the attached arm and element shown in FIG. 21, taken along line 23-23 in FIG. 21, and illustrating the lock in the locked rotation position.
Figure 24:
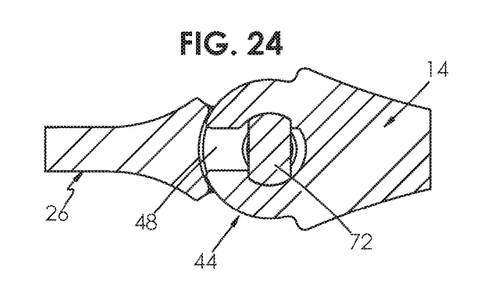
FIG. 24 is a sectional view of the attached arm and element shown in FIG. 22, taken along line 24-24 in FIG. 22, and illustrating the first cam of the lock in the locked rotation position.
Figure 25:
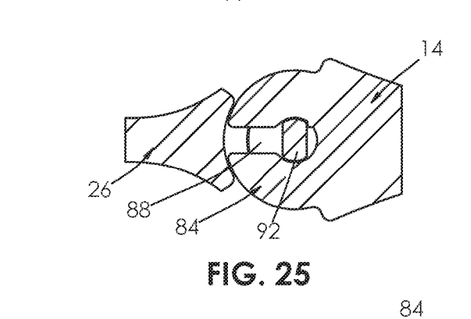
FIG. 25 is a sectional view of the attached arm and element shown in FIG. 22, taken along line 25-25 in FIG. 22, and illustrating the second cam of the lock in the locked rotation position.
Figure 26:
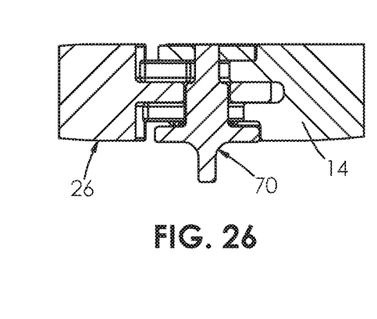
FIG. 26 is a sectional view of the attached arm and element shown in FIG. 21, taken along line 26-26 in FIG. 21, and illustrating the lock in the locked rotation position.

The lock further includes a second cam 92 that is spaced from the first cam 72 (and optionally axially spaced from the first cam) (e.g., FIG. 14). The second cam 92 is configured in a manner similar to that of the first cam 72 such that (1) when the lock 70 is in the release position, the end portion 60 of the second connector structure 42 can be moved to the connected position with respect to the first connector structure 40 with the second cam 92 passing through the second pin slot 88 and into second lock well 90 of the first connector structure, and (2) when the lock is in the lock position the second cam engages the second end portion 84 of the first connector structure to resist withdrawal of the second end portion of the first connector structure from the second connector structure. In embodiments, the second pin slot 88 has a first dimension D5 (e.g., FIG. 4) and the second lock well 90 has a diameter D6 (e.g., FIG. 7) that is greater than the first dimension D5 of the second pin slot. The second cam 92 of the lock 70 has first and second diameters D7 and D8 (e.g., FIGS. 16, 17). The first diameter D7 of the second cam 92 is less than the first dimension D5 of the second pin slot 88, such that when the lock is in the release position the second cam can pass through the second pin slot when the first cam 72 is passing through the first pin slot 48 of the first end portion 44. The second diameter D8 of the second cam 92 is greater than the first dimension D5 of the second pin slot 88, and optionally slightly less than the diameter D6 of the second lock well 90, to enable the second cam to rotate to the lock position in the second lock well. In the illustrated embodiment the lock 70 is configured such that the first cam 72 is larger than the second cam 92. In the illustrated embodiments the first dimension D5 of the second pin slot 88 is less than the first dimension D1 of the first pin slot 48, and the diameter D6 of the second lock well 90 is less than the diameter D2 of the first lock well 50. In embodiments, the second end portion 84 includes a structure, such as stop tab 94 that extends into the second lock well 90 (e.g., FIG. 6), to limit the range of rotation of the second cam 92 between the release and lock positions. In the illustrated embodiment the stop tab 94 will limit the range of rotation of the lock 70 to about 90°.

In embodiments, the first connector structure 40 or second connector structure 42 is on an end of a retractor arm such as 14, and optionally on an end of a sternal retractor arm, a self-retaining retractor arm, or a spinal retractor arm (e.g., a so-called Adson retractor). The retractor arms 14 can include (1) only radiolucent material, (2) only radiodense material, or (3) both of radiolucent and radiodense material. In embodiments, the second connector structure 42 includes (1) only radiolucent material, (2) only radiodense material, or (3) both of radiolucent and radiodense material. In yet other embodiments, the first connector structure 40 includes (1)

only radiolucent material, (2) only radiodense material, or (3) both of radiolucent and radiodense material, and the second connector structure 42 includes (1) only radiolucent material, (2) only radiodense material, or (3) both of radiolucent and radiodense material. Embodiments of the invention include packaged sterile retractor arms such as 14 having the first or second connector structures of the types described above, and optionally different types (e.g., left and right) and sizes of such arms.

Figures 28, 39, 40, 41, 42:
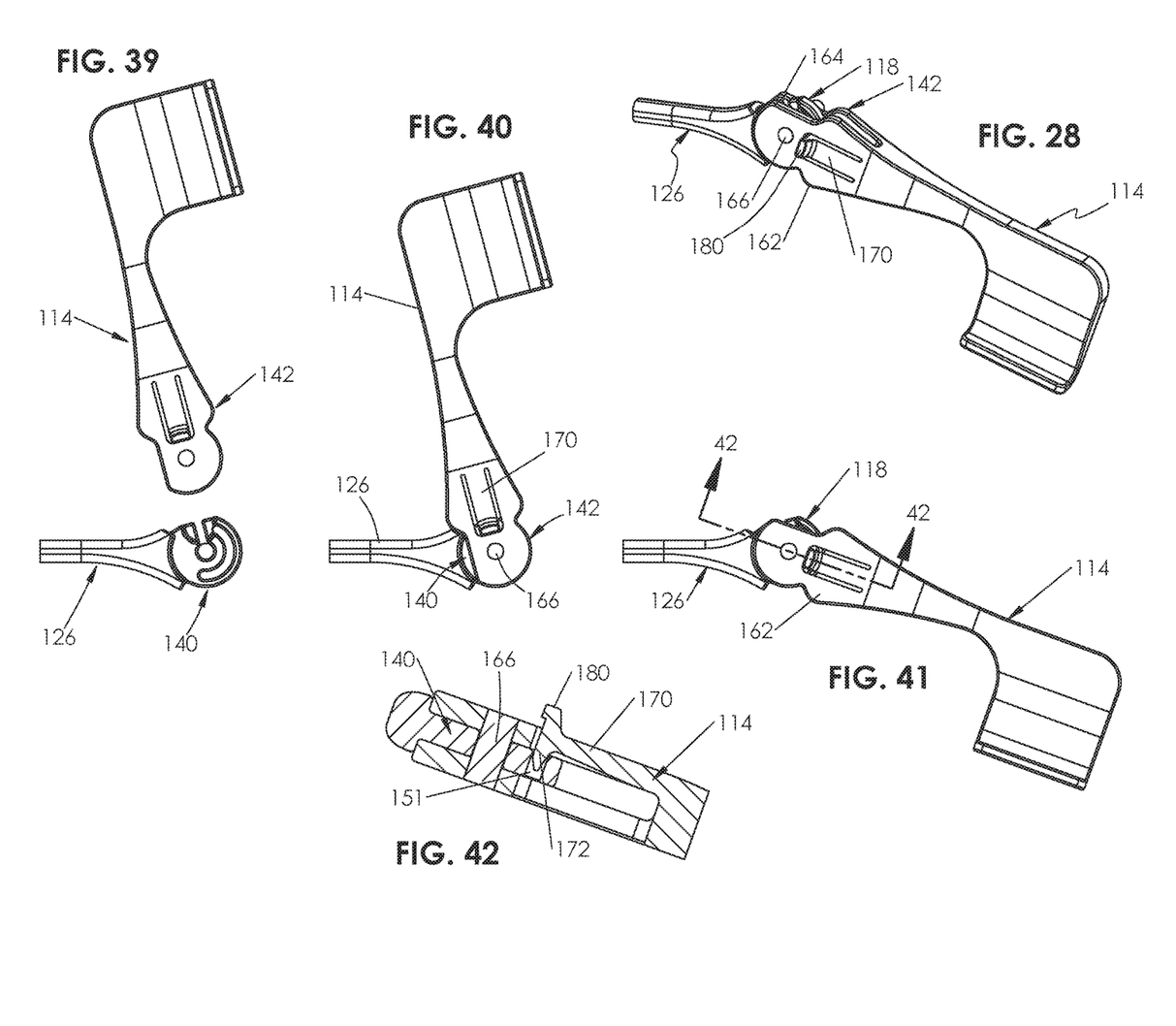
FIG. 28 is an isometric view of a second embodiment of an arm, element and connector structure of the retractor shown in FIG. 1.
FIG. 39 is a side view of the arm and connector structure shown in FIG. 33 and the element and connector structure shown in FIG. 28 disconnected from one another and oriented for attachment.
FIG. 40 is a side view of the arm and connector structure and the element and connector structure shown in FIG. 39, with the arm connector structure inserted into the element connector structure at a pushed in position.
FIG. 41 is a side view of the arm and connector structure and the element and connector structure shown in FIG. 40 at a connected position.
FIG. 42 is a sectional view of the connected arm and element, taken along line 42-42 in FIG. 41.
Figure 29:
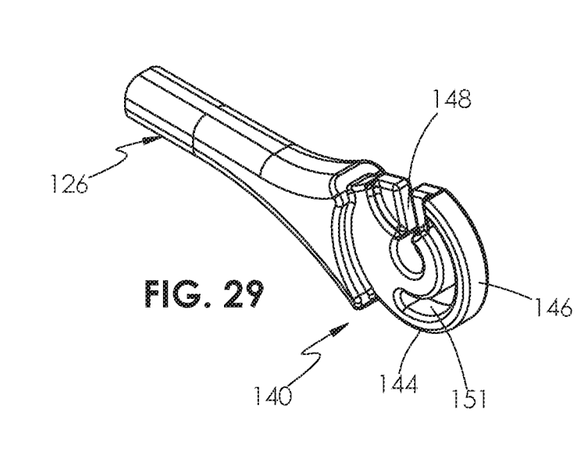
FIG. 29 is an isometric view of the element shown in FIG. 28, illustrating the connector structure on the distal end of the element. The other element and connector structure of the retractor shown in FIG. 1 can be a mirror image of the element and connector structure shown in FIG. 29.
Figure 30:
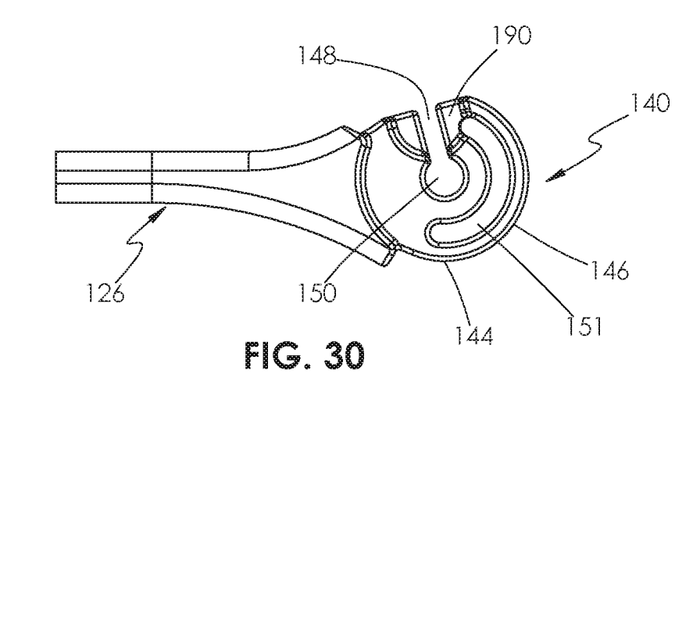
FIG. 30 is a side view of the element and connector structure shown in FIG. 29, illustrating the side shown in FIG. 29.
Figure 31:
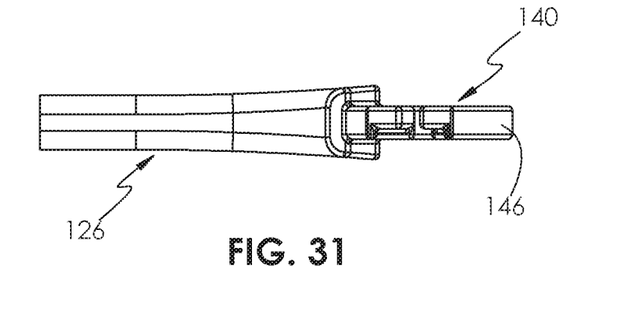
FIG. 31 is a top edge view of the element and connector structure shown in FIG. 29, illustrating the edge shown in FIG. 29.
Figure 32:
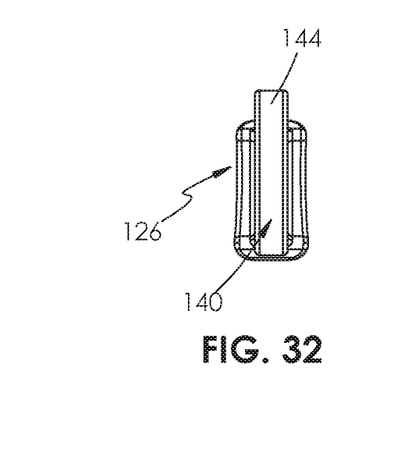
FIG. 32 is an end view of the element shown in FIG. 29, illustrating the end shown in FIG. 29.
Figure 33:
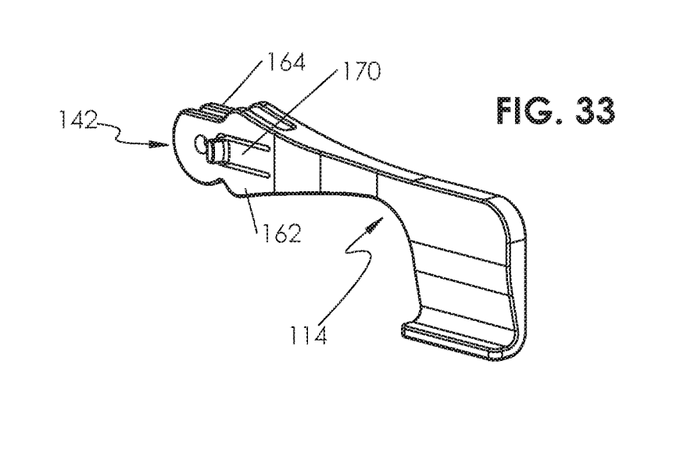
FIG. 33 is an isometric view of the arm shown in FIG. 28, illustrating the connector structure on the proximal end of the arm. The other arm of the retractor shown in FIG. 1 can be a mirror image of the arm shown in FIG. 33.
Figure 34:
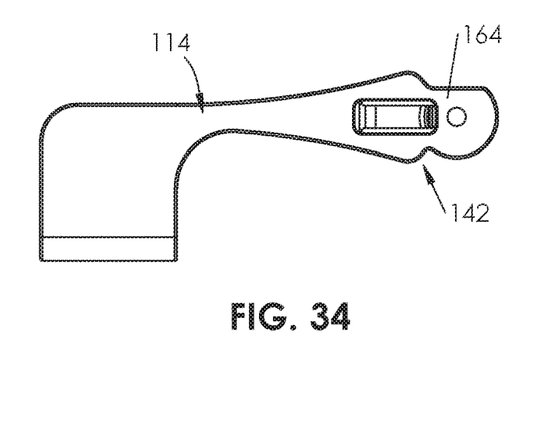
FIG. 34 is a side view of the arm shown in FIG. 33, illustrating a side of the arm opposite the side shown in FIG. 33.
Figures 35, 36:
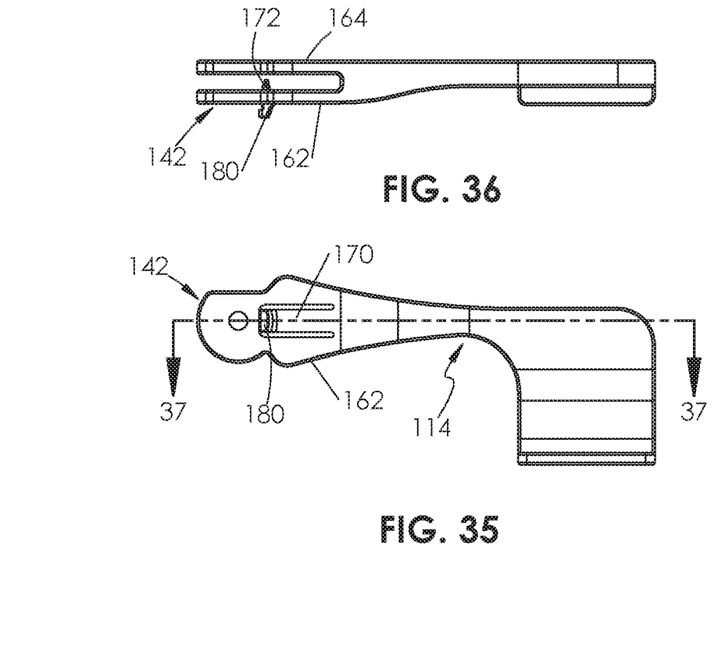
FIG. 35 is a side view of the arm shown in FIG. 33, illustrating the side of the arm shown in FIG. 33.
FIG. 36 is a top edge view of the arm shown in FIG. 33, illustrating the edge shown in FIG. 33.
Figure 37:
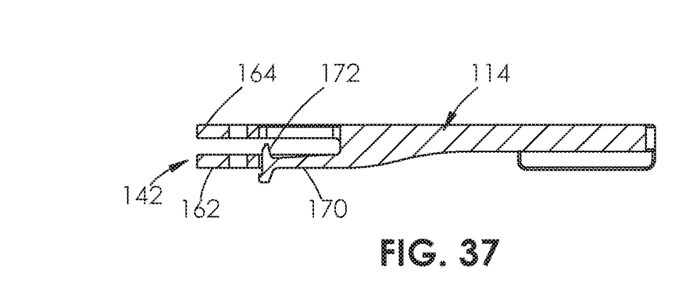
FIG. 37 is a cross sectional view of the arm shown in FIG. 35, taken along line 37-37 in FIG. 35.
Figure 38:
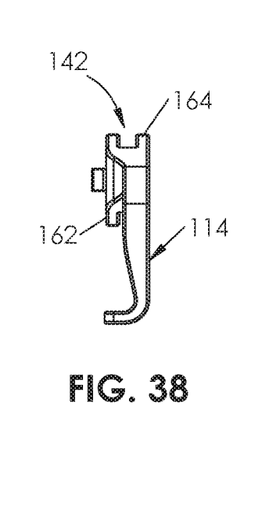
FIG. 38 is an end view of the arm shown in FIG. 33.

FIG. 28 is an illustration of another arm 114, element 126 and connector 118 in accordance with embodiments of the invention. Other features of arm 114, element 126 and connector 118 can be described with reference to FIGS. 29-42. Although one arm 114 and element 126 are described below, the arms and elements can be mirror images of one another.

The connector 118 includes a first connector structure 140 on one of the element 126 or arm 114, and a second connector structure 142 on the other of the element or arm. In the illustrated embodiments (e.g., FIGS. 29-32), the first connector structure 140 is on a distal end of the element 126 and includes an end portion 144 having an edge 146, a pin slot 148 extending into the end portion from the edge, a well or seat 150 in the pin slot, and an engagement slot 151 between the edge and the seat. In embodiments, the edge 146 and engagement slot 151 are arcuate, and a surface of the end portion 144 adjacent to the edge, pin slot 148 and seat 150 is recessed in the proximal end of the arm 114. The first end portion 144 is generally arcuate or circular and the engagement slot 151 is generally arcuate in the illustrated embodiment to facilitate the rotational movement and positioning of the arm 114 with respect to the element 126. In the illustrated embodiments the engagement slot 151 extends through the end portion 144. In other embodiments the engagement slot 151 is a recessed structure in the end portion 144.

In the illustrated embodiments (e.g., FIGS. 33-37) the second connector structure 142 is on a proximal end of the arm 114 and includes first and second spaced-apart joint supports 162 and 164 on the second connector end portion. The first and second joint supports 162 and 164 are configured to receive the first connector structure 140 therebetween at a connected position. A pin 166 extends between the first and second joint supports 162 and 164. An engagement flex arm 170 is on the first joint support 162. The engagement flex arm 170 includes an engagement member 172 on the side facing the first connector structure 142. As shown (e.g., FIGS. 39-42), the pin 166, engagement flex arm 170 and engagement member 172 are configured such that during attachment of the second connector structure to the first connector structure (1) the pin passes through the pin slot 148 and into the seat 150, (2) the engagement flex arm 172 is elastically deflected from its neutral or undeflected position (i.e., away from the first connector structure 140) and the engagement member passes over the first connector structure between the edge 146 and the engagement slot 151. When the first connector structure 140 and second connector structure 142 are at the connected position, the engagement flex arm 172 springs back toward the undeflected position, causing the engagement member 172 to extend into the engagement slot 151.

In the illustrated embodiment the engagement slot 151 is elongated and concentrically located around the seat 150. The second connector structure 142 and arm 114 can rotate about the axis of the pin 166 on the first connector structure 140 and element 126 when the arm is attached to the element with the first and second connector structures at the connected position. Embodiments also include an engagement lift 180 on the engagement flex arm 170. The engagement lift 180 is located on the side of the engagement flex arm 170 opposite the first connector structure 140, and is configured to be grasped by a user to enable the user to deflect the engagement flex arm (e.g., by pulling) and remove the engagement member 172 from the engagement slot 151 during removal of the arm 114 and its second connector structure 142 from the element 126 and its first connector structure 140.

In embodiments, the first connector structure 140 includes a tapered lead in surface 190 between the edge 146 and the engagement slot 151. The lead in surface 190 engages the engagement member 172 and deflects the engagement flex arm 170 to guide the engagement member into the engagement slot 151 during attachment of the second connector structure 142 to the first connector structure 140. In the illustrated embodiments, the lead in surface 190 is located on the sides of the pin slot 148. In this embodiment, the arm 114 is attached to the element 126 by aligning the pin 166 and engagement member 172 with the pin slot 148, and moving the arm to move the pin and engagement member into the pin slot (e.g., FIG. 39). When the arm 114 is attached to the element 126 at the pushed in position by this action, the engagement member 172 will be located in the pin slot 148 on the lead in surface 190. The user will then rotate the arm 114 toward the engagement slot 151, causing the engagement flex arm 170 to deflect and the engagement member 172 to be guided toward the engagement slot. With sufficient rotation of the arm 114, the engagement member 172 will be located over the engagement slot 151, and the engagement flex arm will move toward its undeflected position and snap into the engagement member into the engagement slot 151, thereby causing the arm and element 126 to be in the connected position. The arm 114 can then rotate in the seat 150, with the engagement member 172 in the engagement slot 151 to retain the arm and element 26' in the connected position.

In operation, right and left arms such as 114 will be provided to the OR sterile. OR staff will follow aseptic handling procedures to remove the arms from the sterile package and place onto the sterile field. The staff will select one arm and fit the two sides of the joint (e.g., second connector structure 142) and the female arm 114 about the male joint (e.g., first connector structure 140) of the arm (e.g., element 126). The shaft (e.g., pin 166) in the arm 114 must be aligned with the shaft slot (e.g., pin slot 148). The joint/shaft is lowered down the shaft slot until the shaft is seated in the shaft seat 150. This is the position for use. Once the arm(s) are lowered so the shaft comes to rest in the seat, the arm can be rotated forward (clock wise). This action will cause the lead in feature on the engagement member 172 to interact with the engagement lead in 190 of the metal joint. This action lifts the engagement member by mean of elastic flexing of the engagement flex arm 170. This allows the engagement member to ride over the surface of the male joint between the shaft slot and the engagement slot 151. When the engagement member fully reaches the engagement slot the elastic force (kinematic energy) in the engagement flex arm will push the engagement member into the engagement slot. With the engagement member residing in the engagement slot the arm is secured to the metal handle portion of the device. The radial design of the engagement slot allows the arm to be rotated (e.g., 200 degrees) during use. When the procedure is done or if the surgeon desires a different arm/blade design, perhaps deeper blade, the staff applies a radial lifting force with their finger to the engagement lift 180. This force will apply a torque to the engagement flex arm, and when sufficient torque is applied the engagement member will be raised out of the engagement slot, and with rotation of the arm the arm can be returned to the insertion positon for removal.

Embodiments of the invention offer important advantages. They can, for example, allow x-ray and other imaging of target tissues. They can incorporate the use of metals outside of the target, thereby providing strength, reuse and other high-quality functionality. The ability to efficiently attach and detach various sizes and configurations of arms and blades offers efficiencies by saving the surgeon time and providing optimal fitting to the patient and procedural needs. For example, the device can be configured for pediatric, adolescent and adult patients. The retractors can accommodate both radiolucent (e.g., polymer) and radiodense (e.g., titanium, stainless steel) arms and blades.

Although the invention has been described with reference to preferred embodiments, those of skill in the art will recognize that changes can be made in form and detail without departing from the spirit and scope of the invention.

What is claimed is:

1. A retractor, comprising:
   a retractor element;
   a retractor arm releasably connectable to the retractor element;
   a first connector structure on one of the retractor element and the retractor arm, the first connector structure including:
   a first end portion having a first edge;
   a first pin slot extending into the first end portion from the first edge of the first end portion; and
   a first lock well in the first pin slot; and
   a second connector structure on the other of the element and the arm, the second connector structure including:
   an end portion having an aperture, the end portion configured to receive the first connector structure at a connected position with the aperture aligned with the first lock well of the first connector structure; and
   a lock in the aperture that is rotatable between a release position and a lock position, wherein the lock includes a first cam and is configured such that (1) when the lock is in the release position the end portion of the second connector structure can be moved to the connected position with respect to the first connector structure with the first cam passing through the first pin slot and into the first lock well of the first connector structure, and (2) when the lock is in the lock position the first cam engages the first end portion of the first connector structure to resist withdrawal of the first end portion of the first connector structure from the second connector structure.

2. The retractor of claim 1 wherein:
   the first pin slot has a first dimension;
   the first lock well has a diameter that is greater than the first dimension of the first pin slot; and
   the first cam of the lock has first and second diameters, wherein (1) the first diameter of the first cam is less than the first dimension of the first pin slot, such that when the lock is in the release position the first cam can pass through the first pin slot, and (2) the second diameter of the first cam is greater than the first dimension of the first pin slot, to enable the first cam to rotate to the lock position in the first lock well.

3. The retractor of claim 1 wherein at least one of the first and second connector structures includes stop structure limiting rotation of the lock between the release and lock positions.

4. The retractor of claim 3 wherein the stop structure includes a stop tab extending into the first lock well of the first connector structure.

5. The retractor of claim 1 wherein the first and second connector structures are configured to enable rotation of the arm with respect to the element when the arm and element are connected and the lock is in the lock position.

6. The retractor of claim 1 wherein the lock further includes a knob that can be grasped by a user to rotate the lock.

7. The retractor of claim 1 wherein the first lock well is generally circular.

8. The retractor of claim 1 wherein the first connector structure further includes:
   a second end portion having a second edge, wherein the second end portion is spaced from the first end portion of the first connector structure so as to be on a side of the end portion of the second connector structure opposite the first end portion of the first connector structure when the first connector structure is connected to the second connector structure; and
   a second pin slot extending into the second end portion from the second edge of the second end portion, wherein when the lock is in the release position the end portion of the second connector structure can be moved to the connected position with respect to the first connector structure with the lock passing through the second pin slot.

9. The retractor of claim 8 wherein:
   the first connector structure further includes a second lock well in the second pin slot; and
   the lock further includes a second cam that is spaced from the first cam and is configured such that (1) when the lock is in the release position the end portion of the second connector structure can be moved to the connected position with respect to the first connector structure with the second cam passing through the second pin slot and into second lock well of the first connector structure, and (2) when the lock is in the lock position the second cam engages the second end portion of the first connector structure to resist withdrawal of the second end portion of the first connector structure from the second connector structure.

10. The retractor of claim 9 wherein:
    the second pin slot has a first dimension;
    the second lock well has a diameter that is greater than the first dimension of the second pin slot; and
    the second cam of the lock has first and second diameters, wherein (1) the first diameter of the second cam is less than the first dimension of the second pin slot, such that when the lock is in the release position the second cam can pass through the second pin slot when the first cam is passing through the first pin slot of the first end portion, and (2) the second diameter of the second cam is greater than the first dimension of the second pin slot to enable the second cam to rotate to the lock position in the second lock well.

11. The retractor of claim 10 wherein:
    the lock is configured such that the first cam is larger than the second cam; and the first pin slot and first lock well of the first end portion of the first connector are larger than the second pin slot and second lock well of the second end portion of the first connector.

12. The retractor of claim 11 and further including a stop tab in the second lock well of the first connector structure to limit rotation of the lock between the release and lock positions.

13. The retractor of claim 10 wherein the second lock well is generally circular.

14. The retractor of claim 1 wherein:
the first connector structure is on the end of the retractor arm; and
the second connector structure is on the end of the element.

15. The retractor of claim 14 wherein the retractor arm includes (1) only radiolucent material, (2) only radiodense material, or (3) both of radiolucent and radiodense material.

16. The retractor of claim 1 wherein:
the first connector structure includes (1) only radiolucent material, (2) only radiodense material, or (3) both of radiolucent and radiodense material; and
the second connector structure includes (1) only radiolucent material, (2) only radiodense material, or (3) both of radiolucent and radiodense material.

17. A surgical retractor arm, including:
a proximal end portion configured for attachment to a retractor handle, comprising:
a first end portion having a first edge;
a first pin slot extending into the first end portion from the first edge of the first end portion; and
a first lock well in the first pin slot; and
a distal end portion comprising a blade.

18. The surgical retractor arm of claim 17 wherein:
the first pin slot has a first dimension; and
the first lock well has a diameter that is greater than the first dimension of the first pin slot.

19. The surgical retractor arm of claim 18, the proximal end portion further comprising:
a second end portion having a second edge, wherein the second end portion is spaced from the first end portion;
a second pin slot extending into the second end portion from the second edge of the second end portion; and
a second lock well in the second pin slot.

20. The surgical retractor arm of claim 19 wherein:
the second pin slot has a first dimension that is less than the first dimension of the first pin slot; and
the second lock well has a diameter that is greater than the first dimension of the second pin slot and less than the diameter of the first lock well.

21. The surgical retractor arm of claim 17, wherein the surgical retractor arm is a first retractor arm, and further comprising a second surgical retractor arm, wherein the second surgical retractor arm is configured as a mirror image of the first retractor arm and includes:
a proximal end portion configured for attachment to a retractor handle, comprising:
a first end portion having a first edge;
a first pin slot extending into the first end portion from the first edge of the first end portion; and
a first lock well in the first pin slot; and
a distal end portion comprising a blade.

22. The invention of claim 21, wherein:
the first pin slot of each of the first and second surgical retractor arms has a first dimension; and the first lock well of each of the first and second surgical retractor arms has a diameter that is greater than the first dimension of the first pin slot.

23. The invention of claim 22, wherein the proximal end portions of both the first and second surgical retractor arms further comprise:
a second end portion having a second edge, wherein the second end portion is spaced from the first end portion;
a second pin slot extending into the second end portion from the second edge of the second end portion; and
a second lock well in the second pin slot.

24. The invention of claim 23, wherein:
the second pin slot of each the first and second surgical retractor arms has a first dimension that is less than the first dimension of the first pin slot; and
the second lock well of each of the first and second surgical retractor arms has a diameter that is greater than the first dimension of the second pin slot and less than the diameter of the first lock well.

25. A first component for a surgical retractor, wherein the first component is configured to receive a first end portion of a second component having a first pin slot extending into the first end portion and a first lock well in the first pin slot, the first component comprising:
a first retractor component end portion having an aperture, the first retractor component end portion configured to receive the first end portion of the second component at a connected position with the aperture aligned with the first lock well of the second component; and
a lock in the aperture that is rotatable between a release position and a lock position, wherein the lock includes a first cam and is configured such that (1) when the lock is in the release position the first end portion of the second component can be moved to the connected position with respect to the first component with the first cam passing through the first pin slot and into the first lock well of the second component, and (2) when the lock is in the lock position the first cam engages the first end portion of the second component to resist withdrawal of the first retractor component end portion from the second component.

26. The first component of claim 25, wherein the first pin slot of the second component has a first dimension and the first lock well of the second component has a diameter that is greater than the first dimension of the first pin slot, and wherein: the first cam of the lock further comprises first and second diameters, and wherein (1) the first diameter of the first cam is less than the first dimension of the first pin slot, such that when the lock is in the release position the first cam can pass through the first pin slot, and (2) the second diameter of the first cam is greater than the first dimension of the first pin slot, to enable the first cam to rotate to the lock position in the first lock well of the second component.

27. The first component of claim 25, wherein the first component is further configured to receive a second end portion of the second component, the second end portion spaced from the first end portion of the second component and having a second pin slot extending into the second end portion and a second lock well in the second pin slot, and wherein the lock of the first component further comprises:
a second cam that is spaced from the first cam and is configured such that (1) when the lock is in the release position the second end portion of the second component can be moved to the connected position with respect to the first component with the second cam passing through the second pin slot and into second lock well of the second component, and (2) when the lock is in the lock position the second cam engages the second end portion of the second component to resist withdrawal of the second end portion of the first retractor component end portion from the second component.

28. The first component of claim 27 wherein the first pin slot of the second component has a first dimension and the first lock well of the second component has a diameter that is greater than the first dimension of the first pin slot, and the second pin slot has a first dimension and the second lock well has a diameter that is greater than the first dimension of the second pin slot, and wherein:

the first cam of the lock further comprises first and second diameters, and wherein (1) the first diameter of the first cam is less than the first dimension of the first pin slot, such that when the lock is in the release position the first cam can pass through the first pin slot, and (2) the second diameter of the first cam is greater than the first dimension of the first pin slot, to enable the first cam to rotate to the lock position in the first lock well of the second component; and the second cam of the lock has first and second diameters, wherein (1) the first diameter of the second cam is less than the first dimension of the second pin slot, such that when the lock is in the release position the second cam can pass through the second pin slot when the first cam is passing through the first pin slot of the first end portion, and (2) the second diameter of the second cam is greater than the first dimension of the second pin slot to enable the second cam to rotate to the lock position in the second lock well.

29. The first component of claim 28 wherein the lock is configured such that the first cam is larger than the second cam.

\* \* \* \* \*